United States Patent
Mustonen

(12)
(10) Patent No.: US 6,362,889 B1
(45) Date of Patent: Mar. 26, 2002

(54) IMAGING SYSTEM FOR HIGH-SPEED PAPER WEBS

(75) Inventor: Markku Mustonen, Lawrenceville, GA (US)

(73) Assignee: Conmark, Inc., Lawrenceville, GA (US)

( * ) Notice: Subject to any disclaimer, the term of this patent is extended or adjusted under 35 U.S.C. 154(b) by 0 days.

(21) Appl. No.: 09/598,504

(22) Filed: Jun. 22, 2000

(51) Int. Cl.$^7$ ............................................... G01N 21/84
(52) U.S. Cl. ...................................................... 356/428
(58) Field of Search ................................ 356/429, 430, 356/237.1, 238.1, 238.2, 237.2; 348/125, 126, 128, 96, 98, 97, 82, 86, 88, 92; 382/111, 108, 112, 135, 141

(56) References Cited

U.S. PATENT DOCUMENTS

| | | | | |
|---|---|---|---|---|
| 4,521,089 A | * | 6/1985 | Bohl et al. | 350/582 |
| 4,972,091 A | * | 11/1990 | Cielo et al. | 250/562 |
| 5,394,208 A | * | 2/1995 | Campbell | 354/75 |
| 5,831,668 A | * | 11/1998 | Hirvonen et al. | 348/83 |
| 5,903,306 A | * | 5/1999 | Heckendorn et al. | 348/85 |
| 5,992,245 A | * | 11/1999 | Takei et al. | 73/865.5 |

* cited by examiner

Primary Examiner—Frank G. Font
Assistant Examiner—Michael P. Stafira
(74) Attorney, Agent, or Firm—Rodgers & Rodgers

(57) ABSTRACT

An imaging device for detecting breaks in the paper manufacturing process wherein a camera is disposed adjacent the paper web and is enclosed in a housing. Air under pressure flows through said housing across the lens of the camera so as to prevent accumulation of debris thereon.

3 Claims, 1 Drawing Sheet

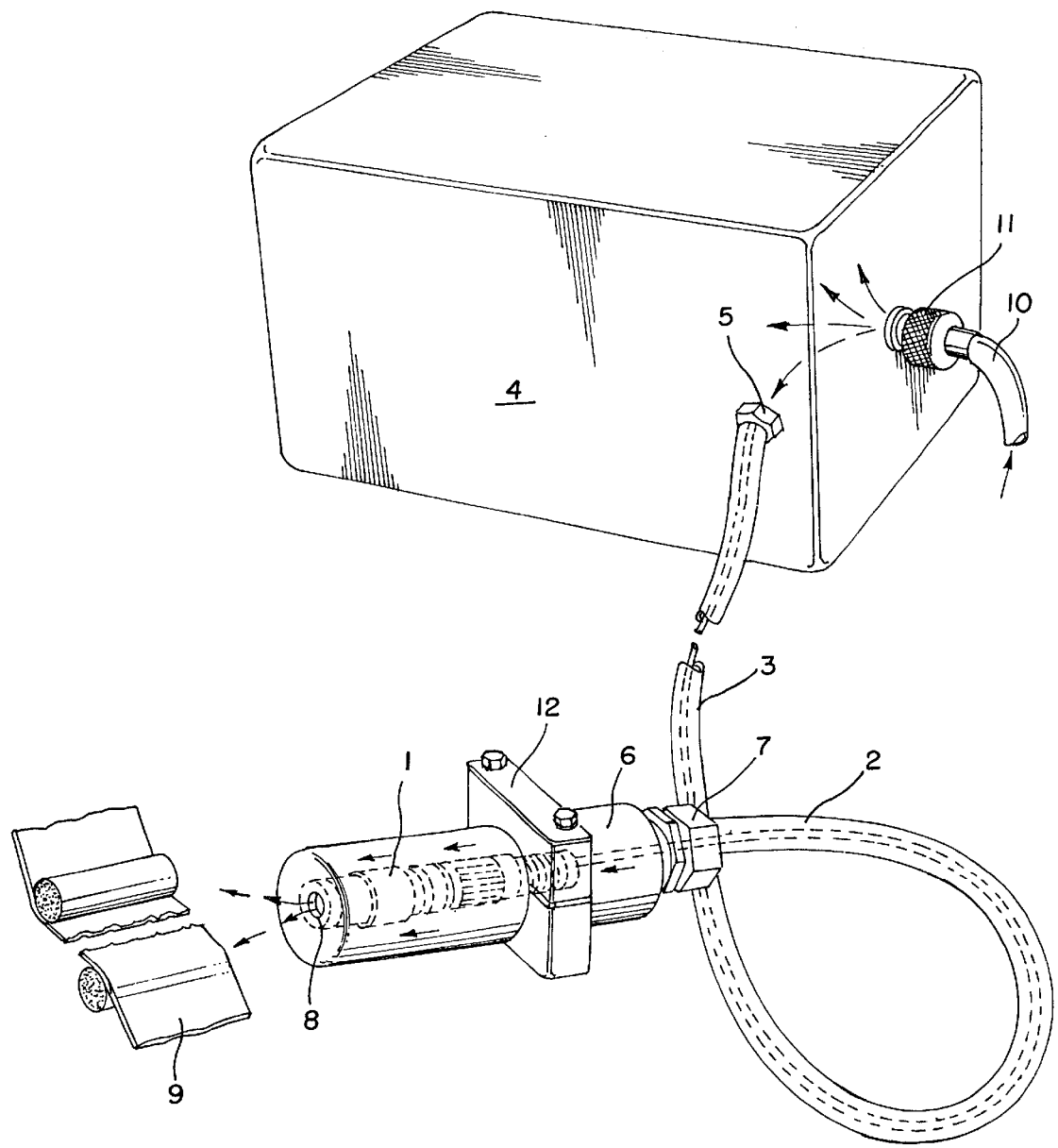

IMAGING SYSTEM FOR HIGH-SPEED PAPER WEBS

BACKGROUND OF THE INVENTION

In the paper making industry, web breaks are quite costly due to the attendant machine downtime. Systems for detecting web breaks typically include camera means which provides the operator with a visual indication of a break. Of course, in the paper making process, the surrounding environment is filled with wet and dry paper fibers. This causes the camera lens to become coated with fibers thereby eliminating the desired visual image. When this occurs, the camera lens must be wiped clean only to be covered again within a typically short period of time.

SUMMARY OF THE INVENTION

By this invention, web imaging means for continuous monitoring of the web includes an imaging device which is enclosed in a housing having an open end thereof. A stream of air is introduced into the housing and exits through the opening to provide a continuous flow of air past the imaging device thereby prevent; accumulation of debris on the device.

BRIEF DESCRIPTION OF THE DRAWING

The single FIGURE drawing is a partially schematic representation of the imaging system according to this invention.

DESCRIPTION OF THE PREFERRED EMBODIMENT

In the drawings, the numeral 1 designates the system imaging device one component of what is known in the trade as a lipstick camera. One camera which has been found to be compatible with this invention is PANASONIC lipstick camera marketed under model number GP-KS162. This invention is also well suited to applications wherein the imaging device includes infrared detection means.

Cable 2 extends from one end of camera 1 through flexible tube 3 to the central control unit for camera 1 as shown schematically in the drawing and indicated by the numeral 4. Flexible tube 3 is connected to central control unit 4 by means of nut assembly 5 and to camera housing 6 by means of nut assembly 7 as is well known. Aperture 8 is formed in housing 6 at the free end thereof so as to provide an opening through which the lens of camera 1 is able to view the edge of paper web 9.

According to this invention, air is introduced into the system through conduit 10 which is suitably attached to central control unit 4 by conventional coupling means 11. Air, which is under positive pressure, flows from conduit 10 through flexible tube 3, into housing 6 and exists through aperture 8.

Bracket 12 is provided for the purpose of conveniently attaching housing 6 to a structural element of the paper machine so as to attain the desired camera angle. Of course, any suitable attachment means could likewise be employed such as welding and the like.

Therefore, by means of a continuous stream of air passing by the lens of camera 1, any undesirable debris is prevented from settling thereon and obscuring the visual operation of the lens. The operation of web 9 is continually observed without any interruption thereby providing reliable detection of any abnormal movement. Also the constant visual image of any sheet breaks provides a means for analysis to help prevent future breaks. In summary, this invention eliminates costly downtime inherent in existing systems when the camera lens becomes coated with debris requiring the operator to manually clean the lens.

What is claimed is:

1. An imaging system for a paper web comprising an imaging device, said imaging device having a lens and being generally tubular and operably interconnected to a central control unit, said imaging device being enclosed in a tubular housing, said housing comprising first and second ends, an aperture formed in said first end, said lens being in close proximity to said aperture, pressurized air being introduced into said housing through said second end wherein said pressurized air flows by said imaging device and exits through said aperture, said imaging device being interconnected to said central control unit by means of a cable, said cable being disposed within a flexible tube, said flexible tube being interconnected to said housing at one end thereof and to said central control unit at the other end thereof, and said pressurized air constantly flowing from said central control unit to said aperture through said flexible tube.

2. An imaging device according to claim 1 wherein said imaging device is a video camera.

3. An imaging device according to claim 1 wherein the diameter of said housing is slightly larger than the diameter of said imaging device.

* * * * *